United States Patent [19]
Goldscher

[11] Patent Number: 5,679,781
[45] Date of Patent: Oct. 21, 1997

[54] PROCESS FOR THE MANUFACTURE OF ISOMALTITOL

[75] Inventor: Rivka Labin Goldscher, Hafia, Israel

[73] Assignee: Gadot Biochemical Industries Ltd., Haifa Bay, Israel

[21] Appl. No.: 489,027

[22] Filed: Jun. 9, 1995

[30] Foreign Application Priority Data

Jun. 26, 1994 [IL] Israel .......................... 110126

[51] Int. Cl.$^6$ ............................................. C07H 1/00
[52] U.S. Cl. ................................ 536/18.5; 536/4.1
[58] Field of Search .................... 539/483; 536/4.1, 536/18.5

[56] References Cited

U.S. PATENT DOCUMENTS

| | | | |
|---|---|---|---|
| 2,868,847 | 1/1959 | Boyers | 536/18.5 |
| 4,233,439 | 11/1980 | Schineck et al. | 536/18.5 |

FOREIGN PATENT DOCUMENTS 1429334  3/1976  United Kingdom .

*Primary Examiner*—Elli Peselev
*Attorney, Agent, or Firm*—Morgan & Finnegan LLP

[57] ABSTRACT

The present invention relates to an improved process for the manufacture of Isomaltitol by hydrogenation of Isomaltulose. According to the process, a solution of Isomaltulose having a concentration in the range of between 20% to 50% by weight, is hydrogenated at a temperature in the range of between 80° C. to 130° C., using a catalyst selected from Ruthenium, Nickel and mixtures thereof on an inert support at a pressure below 50 atmospheres, the pH being maintained in the range of 3 to 8. The resulted product is substantially free from other polymers. Among the advantages of the process it should be mentioned the fact that it enables to achieve the desired ratio between the two isomers α-Glucopyranosyl-1,1-Mannitol (GPM) and α-Glucopyranosyl-1,6-D-Sorbitol (GPS).

6 Claims, 3 Drawing Sheets

PROCESS FOR THE MANUFACTURE OF ISOMALTITOL

The present invention relates to a process for the manufacture of polyols. More particularly, the invention relates to an improved process for the manufacture of Isomaltitol, by hydrogenation of Isomaltulose.

BACKGROUND OF THE INVENTION

Saccharose is considered as the starting material for the manufacture of Isomaltulose. Isomaltulose can be further hydrogenated in an aqueous alkaline or neutral solution, in the presence of a catalyst, to produce Isomaltitol. Platinum and palladium were quite successfully used, as catalysts having the advantage that the respective amount required is less than that necessary for nickel as catalyst. However, all these catalysts exhibit a high efficient conversion, only at a reaction temperature of above 160° C. and a pressure of above 160 atmospheres, which is a serious drawback from a technological point of view.

According to the British Patent Number 1,429,334 Isomaltitol is obtained by the hydrogenation of a solution of Isomaltulose. As mentioned, the starting solution should have a concentration in the range of 35% to 40% by weight, in the presence of Raney Nickel as catalyst, at a pH of at least 9.0, a pressure in the range of 30 to 100 atmospheres and a temperature in the range of 100° to 129° C.

In the German patent number 2,520,173, mixtures of glucopyranosyl-mannitol and glucopyranosyl-sorbitol are obtained from a solution of Isomaltulose having a concentration of above 50% by weight, by hydrogenation in a neutral medium in the presence of Raney Nickel as catalyst at a pressure of about 100 atmospheres.

In the U.S. Pat. No. 2,868,847 it is described a process for the production of polyhydric alcohols by hydrogenation of mono- and disaccharides. The process is carried out at a pressure in the range of 7 to 105 atmospheres and a temperature in the range of 50° to 400° C., using a catalyst selected from the group consisting of ruthenium, ruthenium oxide, or ruthenium mixed with platinum, on carbon or alumina supports.

One of the main disadvantage of all the known methods for obtaining Isomaltitol is the non-selectivity of the hydrogenation in order to obtain the preferred desired ratio between the glucopyranosyl-mannitol and glucopyranosyl-sorbitol. Furthermore, the known hydrogenation of Isomaltulose requires a relatively long reaction time at the very high pressure involved, in order to obtain an optimal yield.

It is an object of the present invention to provide a proces for the manufacture of Isomaltitol by the hydrogenation of Isomaltulose. It is another object of the present invention to provide a process for the manufacture of Isomaltitol, wherein a selected ratio between the two isomeric components (α-D-Glucopyranosyl-1,1-D-Mannitol (hereafter referred to GPM) and α-D-Glucopyranosyl-1,6-D - Sorbitol (hereafter referred to GPS) is obtained.

BRIEF DESCRIPTION OF THE INVENTION

The invention relates to a process for the manufacture of Isomaltitol by the hydrogenation of a solution of Isomaltulose having a concentration in the range of between 20% to 50% by weight, at a temperature between 80° to 130° C., using a catalyst selected from Ruthenium, Nickel and mixtures thereof on an inert support, the pressure exerted being below 50 atmospheres and the pH in the range of between 3 to 8. It was found that under these critical conditions, the Isomaltitol produced is substantially free from other polyols, the hydrogenation being completed after less than about 3 hours. An important advantage of the invention is the fact that it enables to achieve the desired ratio between the two isomeric forms.

DETAILED DESCRIPTION OF THE INVENTION AND FIGURES

Isomaltitol, a polyhydric alcohol consisting of the two polyols mentioned above: GPM and GPS, is obtained according to the present invention at a weight ratio of between 38:62 to 62:38, which is a most preferred product known on the market. The various parameters which influence the hydrogenation reaction, were thoroughly investigated in order to find the main factors which govern this reaction for obtaining the above ratio between the two polyols.

It was surprisingly found according to the present invention that an increase in the reaction temperature to above 130° C., which is mentioned in the prior art, will affect substantially the quality of Isomaltitol product by changing the ratio between said two polyols. Thus, in the above U.S. Pat. No. 2,868,847 (Column 1, lines 67–69) it is suggested to carry out the hydrogenation even at a temperature of above 200° C., pointing out that the high temperatures are useful in a continuous process operation, which is most beneficial in an industrial plant. However, at these high temperatures, there is a danger of caramelization.

Figure 1:
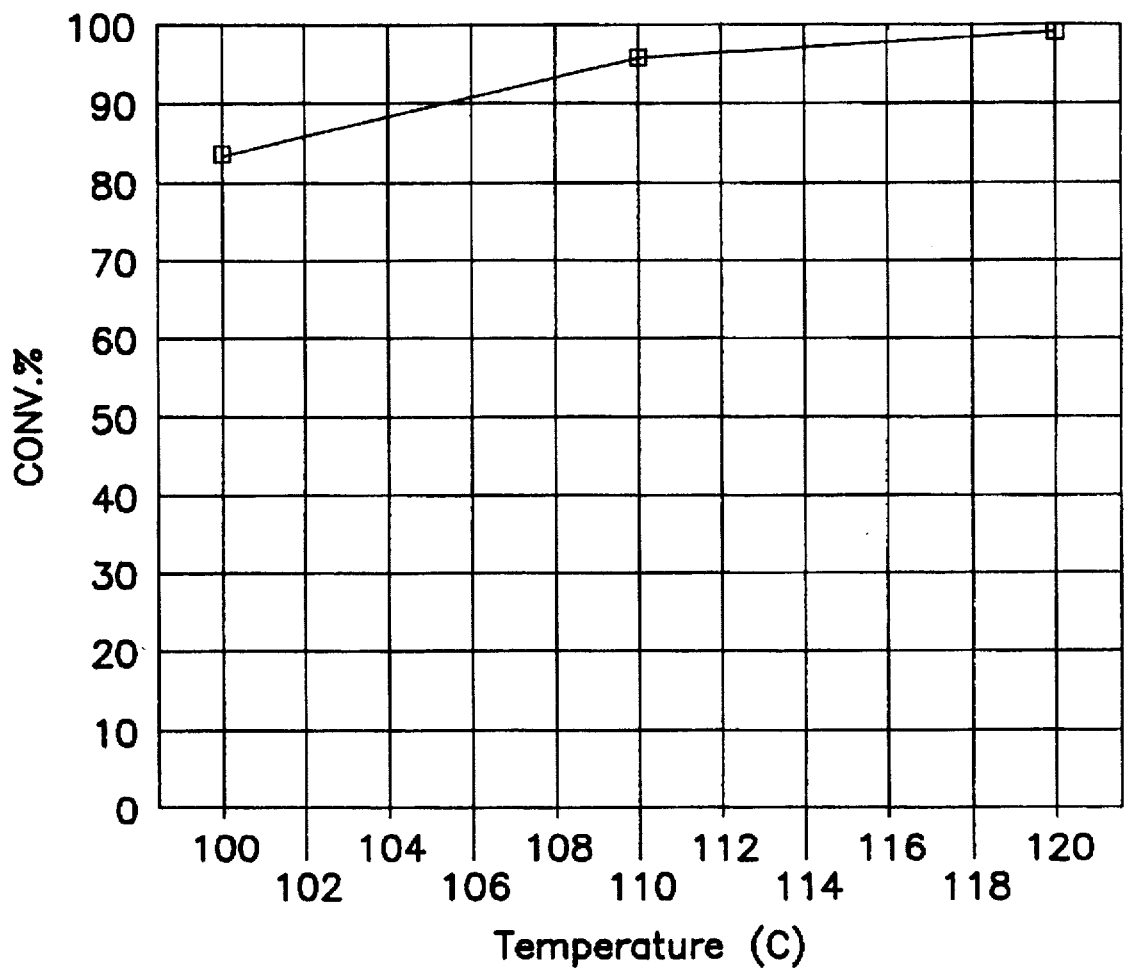
FIG. 1 illustrates the correlation of the conversion of Isomaltulose into Isomaltitol as a function of temperature.

In the attached FIG. 1, it is presented a graph which correlates the extent of conversion of the Isomaltulose into Isomaltitol, as a function of temperature. As can be noticed, at a temperature of 100° C. said conversion is about 82%, reaching more than 99% at a temperature of 1200° C.

Figure 3:
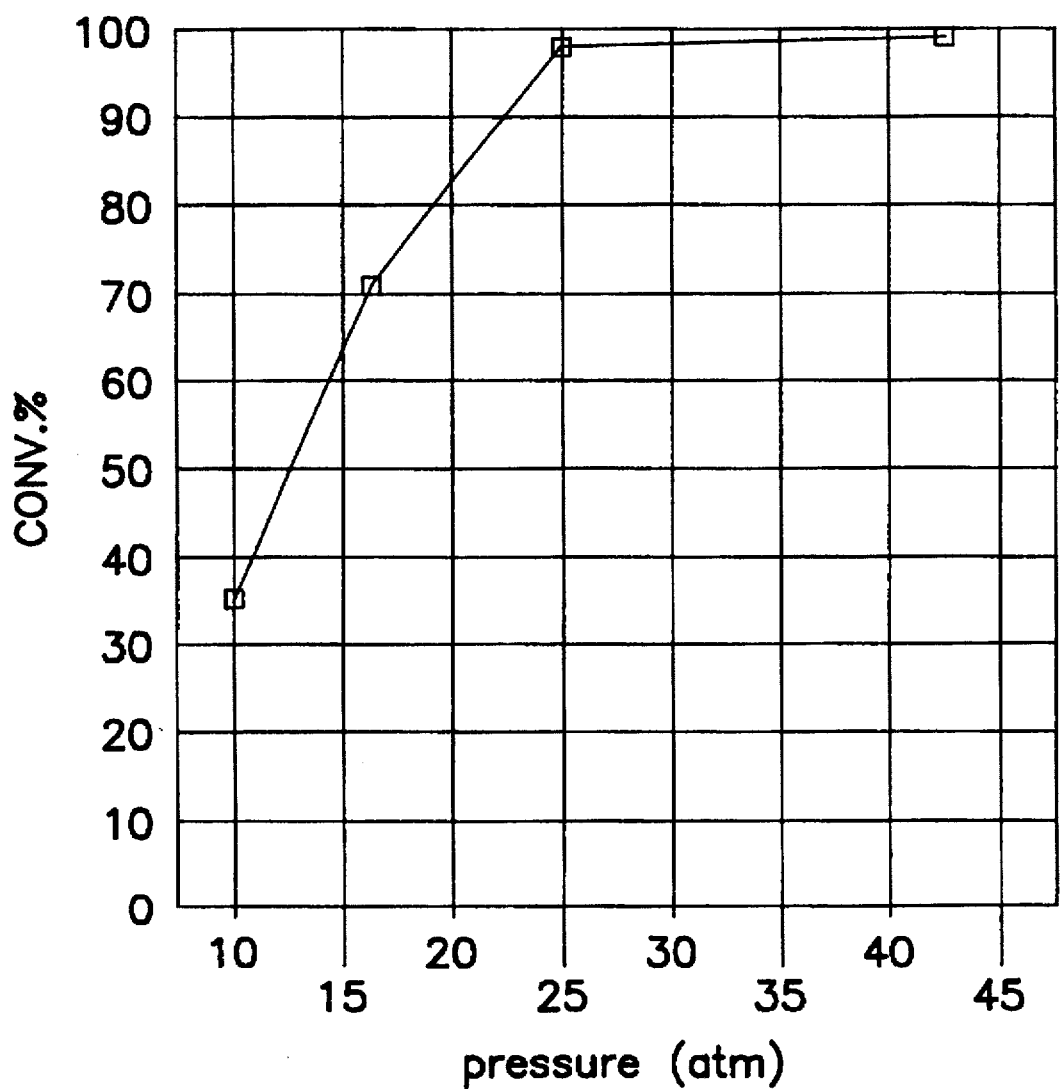
FIG. 3 illustrates the rate of conversion to Isomaltitol as a function of the pressure exerted during the hydrogenation.

It was also found that the use of a pressure below 50 atmospheres, instead of up to 100 atmospheres suggested in the prior art, is sufficient for the system according to the present invention in order to obtain the very high conversion rates. In addition, this is also a significant advantage from a technological point of view. The most preferred pressure was found to be in the range of between 10 to 20 atmospheres. As can be noticed from the FIG. 3 after 45 minutes at a pressure of 20 atmospheres a conversion of about 83% is obtained, while at a pressure of 25 atmospheres, the maximum conversion is achieved.

The particular catalyst used in the hydrogenation, has a significant influence on the reaction. Thus, Platinum and Palladium are mentioned in the prior art to be preferred for this hydrogenation, in view of the small amounts thereof required in the reaction. However, it was found according to the present invention that their use have a bad influence on the ratio between the two polyols of Isomaltitol. The most preferred catalyst useful for the present invention is Ruthenium on an inert support, the amount required being in the range of between 0.28 to 1.1% by weight of the reagents. The Ruthenium may not be absolutely pure and may contain small amounts of other metals. Also a mixture of Ruthenium and Nickel, was found to be useful for said hydrogenation.

Figure 2:
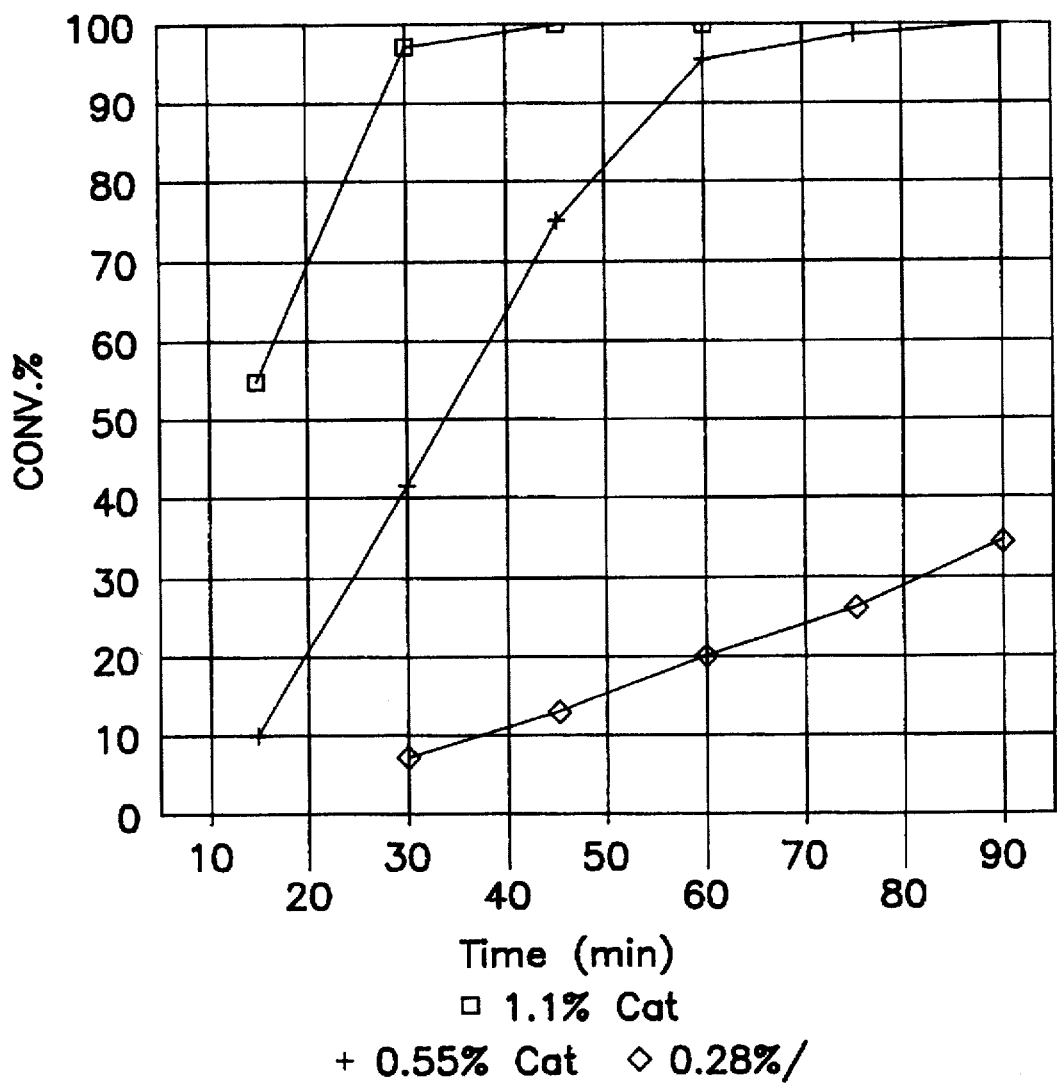
FIG. 2 illustrates the rate of conversion to Isomaltitol as a function of the catalyst amount.

The correlation between the amount of catalyst and the conversion rate appears in a clear manner in the attached FIG. 2, which shows that with an amount of only 0.86% catalyst, a conversion to Isomaltitol of above 85% is obtained. These amounts of catalyst according to the present invention, are much below those utilized with other suggested catalysts, such as Raney Nickel, where the amounts used are in the order of 3% to 10%. Thus, the above U.K Patent Number 1,429,334 mentions in one Example even an amount of 8% of this catalyst.

The inert support for the catalyst may be selected from alumina, carbon, silica, kieselguhr, zeolites and the like, the most preferred being carbon.

Another advantage of the process according to the present invention, is the fact that the pH in the system is between 3 to 8 and generally between 4 to 6, while according to the prior art the pH has to be maintained between 7 to 9 by adding extraneous reagents.

The solution of Isomaltitol is purified, after the filtration of the catalyst residue, by active carbon or by an ion exchange operation. Upon its concentration by evaporation to above 90%, a melt will be obtained which could be further transformed into a crystalline product. The Isomaltitol produced, appears as an odourless, white and non-hygroscopic substance, having a melting point in the range of between 145°–155° C. Being considered as a low-calorie agent and in view of its sweetening property, it is successfully used for many purposes, such as: candies, ice-creams, milk products, baked products, preserved and fruit preparations, etc. Especially, it is used as a dietetic nourishment and food stuff, as well as a carrier for artificial sweeteners.

The invention will be hereafter illustrated by a number of Examples, being understood that these Examples are presented only for a better understanding of the invention without limiting its scope as covered by the appended Claims. A person skilled in the art might insert small deviations in the description as given in said Examples, without being outside the appended claims.

In the following Examples, the concentrations mentioned are given by weight, unless otherwise stated.

EXAMPLE 1

The following reagents were introduced into a stirred autoclave:

325 g Water;

125.6 g Isomaltulose, and 1.58 g Ruthenium on Carbon (on dry basis), as catalyst.

The autoclave was closed, purged with nitrogen and then gaseous hydrogen was introduced up to 16 atmospheres.

The temperature was raised up to 120° C.

The reaction ceased after 60 minutes, a complete conversion to Isomaltitol being obtained, consisting of 42.9% of GPM and 57.1% of GPS.

EXAMPLE 2

The following reagents were introduced into a stirred autoclave:

325 g Water;

125.6 g Isomaltulose, and 1.9 g 5% Ruthenium on Carbon (on dry basis), as catalyst.

The autoclave was closed, purged with nitrogen and then hydrogen was introduced up to 16 atmospheres.

The temperature was raised up to 120° C.

The reaction ceased after 90 minutes, a complete conversion to Isomaltitol being obtained, consisting of 47.8% GPM and 52.2% GPS.

EXAMPLE 3

The following reagents were introduced into a stirred autoclave:

227.6 g Water;

91.4 g Isomaltulose, and 0.86 g 5% Ruthenium on Carbon (on dry basis) and 1.83 g 54% Nickel on Carbon as catalysts.

The autoclave was closed, purged with nitrogen and then hydrogen was introduced up to 16 atmospheres.

The temperature was raised up to 120° C.

The reaction ceased after 120 minutes, a complete conversion to Isomaltitol being obtained, consisting of 56.1% GPM and 43.9% GPS.

EXAMPLE 4

The following reagents were introduced into a stirred autoclave:

275 g Water;

225 g Isomaltulose, and 1.25 g 5% Ruthenium on Carbon (on dry basis) as catalyst.

The autoclave was closed, purged with nitrogen and then hydrogen was introduced up to 16 atmospheres.

The temperature was raised up to 120° C.

The reaction ceased after 45 minutes, a complete conversion to Isomaltitol being obtained, consisting of 46.3% GPM and 53.7% GPS.

EXAMPLE 5

The following reagents were introduced into a stirred autoclave:

443 g Water;

110 g Isomaltulose, and 1.39 g 5% Ruthenium on Carbon (on dry basis) and 0.55 g Nickel (54%) on Carbon as catalysts.

The autoclave was closed, purged with nitrogen and then hydrogen was introduced up to 10 atmosphere.

The temperature was raised up to 120° C.

The reaction ceased after 150 minutes, a complete conversion to Isomaltitol being obtained, consisting of 50.5% GPM and 49.5% GPS.

EXAMPLE 6

The following reagents were introduced into a stirred autoclave:

700 g Water;

300 g Isomaltulose, and 1 g 5% Ruthenium on Carbon (on dry basis) as catalyst.

The autoclave was closed, purged with nitrogen and then hydrogen was introduced up to 14 atmospheres.

The temperature was raised up to 100° C.

The reaction ceased after 90 minutes, a complete conversion to Isomaltitol being obtained, consisting of 44.1% GPM and 55.9% GPS.

I claim:

1. A process for the manufacture of Isomaltitol, a polyhyric alcohol consisting of two polyols, α-D-Glucopyranosyl-1, 6-D-Mannitol (GPM) and α-D-Glucopyranosyl-1, 6-D-Sorbitol (GPS), by hydrogenation of a solution of Isomaltulose having a concentration between 20% and 50% by weight, at a temperature between 80° C. and 130° C., using a catalyst on an inert support, said catalyst selected from the group consisting of ruthenium and a mixture of ruthenium and Nickel, the pressure exerted being below 50 atmospheres and the pH being between 3 and 8, wherein Isomaltitol is obtained having a weight ratio of GPM:GPS between 38:62 and 62:38.

2. The process according to claim 1, wherein said hydrogenation is carried out at a temperature of about 100° C.

3. The process according to claim 1 wherein the pressure prevailing during the hydrogenation is between 10 and 30 atmospheres.

4. The process according to claim 1, wherein the pH in the system is between 4 and 6.

5. The process according to claim 1, wherein the amount of catalyst is between 0.28% and 1.1% by weight of the reactants.

6. The process according to claim 5, wherein said catalyst is on an inert support selected from the group consisting of carbon, silica and alumina.

* * * * *